(12) United States Patent
Gönczi et al.

(10) Patent No.: US 6,573,386 B1
(45) Date of Patent: Jun. 3, 2003

(54) PROCESS FOR THE PREPARATION OF SPIRO[(4-CYCLOHEXANONE)-[3H]INDOL]-2'[1'H]-ONE DERIVATIVES

(75) Inventors: Csaba Gönczi, Budapest (HU); Éva Csikós, Budapest (HU); István Hermecz, Budapest (HU); Gergely Héja, Szentendre (HU); Árpád Illár, Budapest (HU); Lajos Nagy, Szentendre (HU); Andrea Sántáné Csutor, Budapest (HU); Attila Simon, Budapest (HU); Kálmán Simon, Budapest (HU); Ágota Smelkóné Esek, Budapest (HU); Tiborné Szomor, Budapest (HU); Györgyné Szvoboda, Dunakeszi (HU)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/030,648

(22) PCT Filed: Jul. 13, 2000

(86) PCT No.: PCT/HU00/00081

§ 371 (c)(1),
(2), (4) Date: Apr. 17, 2002

(87) PCT Pub. No.: WO01/05760

PCT Pub. Date: Jan. 25, 2001

(30) Foreign Application Priority Data

Jul. 15, 1999 (HU) .............................................. 9902374

(51) Int. Cl.$^7$ ............................................ C07D 209/54
(52) U.S. Cl. ...................................................... 548/411
(58) Field of Search ......................................... 548/411

(56) References Cited

U.S. PATENT DOCUMENTS 3,395,156 A   7/1968   Wolf et al.
5,994,350 A   11/1999  Foulon et al.

FOREIGN PATENT DOCUMENTS

WO    WO 97 15556 A    5/1997

OTHER PUBLICATIONS

R.S. Johnson et al; "The Alkaloids of Gelsenium sempervirens. Part IV. Derivatives of pyridine, isoquinoline, and indol–2(3H)–one as possible initial materials for synthesis of Gelsemine"; Journal of the Chemical Society, Section C: Organic Chemistry; 1970, pp 796–800.

Andrew M. Thompson et al; "Tyrosine Kinase Inhibitors. 1. Structure–Activity Relationships for Inhibition of Epidermal Growth Factor Receptor Tyrosine Kinase Activity by 2,3–Dihydro–2–thioxo–1H–indole–3–alkanoic acids)"; Journal of Medicinal Chemistry, vol. 36, No. 17, 1993, pp 2459–2469.

*Primary Examiner*—Deborah C Lambkin
(74) *Attorney, Agent, or Firm*—Michael D. Alexander; Paul E. Dupont

(57) ABSTRACT

The invention relates to a process for the preparation of spiro [(4-cyclohexanone)-[3H]indol]-2'[1'H]-one derivatives of general formula I—wherein $R^1$ and $R^2$ independently stand for hydrogen, $C_{1-4}$alkyl, $C_{1-4}$alkoxy, $C_{1-4}$alkylthio, $C_{1-4}$polyfluoroalkyl, $C_{1-4}$polyfluoroalkoxy, $C_{3-7}$cycloalkyloxy, $C_{3-7}$cycloalkylthio, phenoxy, benzyloxy or nitro group—, characterized by reacting an indolin-2-one derivative of general formula II—wherein $R^1$ and $R^2$ are as defined above—with a compound capable for introducing a protective group, coupling the compound of general formula III, thus obtained—wherein $R^1$ and $R^2$ are as defined above and A stands for a protective group—with acrylic acid $C_{1-4}$ester; cyclizing the resulting compound of general formula IV—wherein $R^1$ and $R^2$ are as defined above—with a compound capable for introducing a protective group, coupling the compound of formula III thus obtained,—wherein $R^1$ and $R^2$ are as defined above and A stands for a protective group—with an acrylic acid $C^{1-4}$ester, cyclizing the resulting compound of formula IV—wherein $R^1$ and $R^2$ are as defined above $R^3$ stands for $C_{1-4}$alkyl and A stands for a protective group—, eliminating the—$COOR^3$ group and the A protective group of the keto-ester of general formula V—wherein $R^1$ and $R^2$ are as defined above, $R^3$ stands for $C_{1-4}$alkyl and A stands for a protective group—, optionally without isolation of the compounds of general formulae IV and/or V and/or VI.

7 Claims, No Drawings

PROCESS FOR THE PREPARATION OF SPIRO[(4-CYCLOHEXANONE)-[3H]INDOL]-2' [1'H]-ONE DERIVATIVES

This application is a 371 of PCT/HU00/00081, filed Jul. 13, 2000

Spiro[(4-cyclohexanone)-[3H]indol-2'[1'H]-one and dispiro[(1,3-dioxolan)-2,-4'-cyclohexane-3H]indol]-2" [1"H]-one derivatives are important intermediates to the vasopressine $V_2$ antagonistic compound, SR 121463. For example, as described in patent application WO 9715556 the dispiro[(1,3-dioxolan)-2,4'-cyclohexane-1,-3"-(5"-ethoxy)-[3H]indol]-2"[1"H]-one (compound of formula VII)

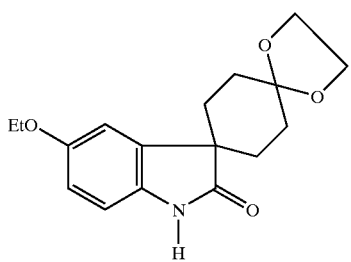

can be prepared by reacting 4-ethoxyphenylhydrazine with 4-(1, 3-dioxolan)cyclohexane-carboxylate sodium salt followed by cyclization of the resulting 1-(4'-ethoxyphenyl)-2-(4"-/1,3-dioxolan/-cyclohexane-carbonyl)-hydrazine.

According to another synthetic route (EP 636608) the compound of formula VII is obtained by oxidation of the spiro[(4-hydroxy-cyclohexane)-1,3'(5'-ethoxy)-[3H]indol-2' [1'H]-one to the appropriate cyclohexanone derivative, from which the ketal of the formula VII is prepared by reaction with ethylene glycol.

Disadvantages of both of the above syntheses are the toxic starting materials, many-step syntheses, low yields of some synthetic steps, expensive reagents and extreme reaction conditions in certain reactions.

To our surprise, we have found that in contrast to the analogous reaction described in the literature (Annalen 1941, 548, 117–146; J. Am. Chem. Soc. 1953, 75, 5301–5305; J. Chem. Soc. C, 1970, 796–800, J. Med. Chem. 1993, 36, 2459–2469) the addition of methyl or ethyl acrylate to 5-ethoxy-indolinone, followed by Dieckmann-condensation, hydrolysis and decarboxylation does not lead to a homogeneous product, that is why the procedures described in the literature above are not suitable for industrial synthesis. We have found that the hydrogen in position-1 of the 5-ethoxy-indolinone has to be substituted by an appropriate protective group, if we want the subsequent reactions to proceed in the desired direction.

In the case the substituent in position-1 is a phenyl group as described in U.S. Pat. No. 3,395,156 side reactions cannot be avoided. Before the Dieckmann-condensation the obtained 1-phenyloxindole-3,3-dipropionic acid ester has to be hydrolyzed and reesterified to get a pure starting material.

The subject of our invention is a process for the preparation of spiro [(4-cyclohexanone)-[3H]indol]-2'[1'H]-one derivatives of the general formula I

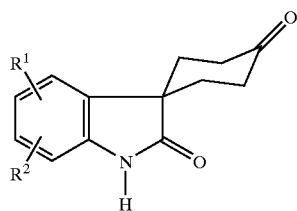

—wherein $R^1$ and $R^2$ independently stand for hydrogen, $C_{1-4}$alkyl, $C_{1-4}$alkoxy, $C_{1-4}$altkylthio, $C_{1-4}$polyfluoroalky, $C_{1-4}$polyfluorbalkoxy, $C_{3-7}$cycloakyloxy, $C_{3-7}$cycloalkylthio, phenoxy, benzyloxy or nitro group—, characterized by reacting an indolin-2-one derivative of the general formula II

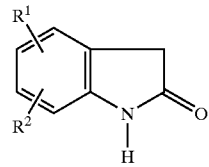

—wherein $R^1$ and $R^2$ are as defined above—with a compound capable for introducing a protective group, selected from 2-tetrahydropyranyl, 1-diethoxy-methylene or $C_{1-4}$alkoxycarbonylethyl group, coupling the compound of general formula III,

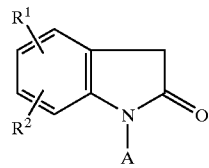

thus obtained—wherein $R^1$ and $R^2$ are as defined above and A stands for a protective group, selected from 2-tetrahydropyranyl, 1-diethoxy-methylene or $C_{1-4}$alkoxycarbonylethyl group—with an acrylic acid $C_{1-4}$ester, cyclizing the resulting compound of the general formula IV

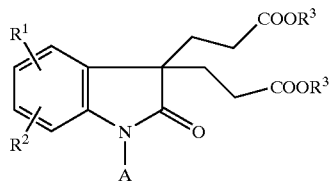

—wherein $R^1$, $R^2$ and A are as defined above, $R^3$ stands for $C_{1-4}$ alkyl group—, eliminating the —COOR$^3$ group and the A protective group of the keto-ester of general formula V

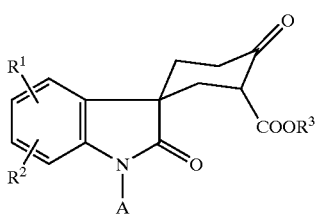

—wherein $R^1$, $R^2$, $R^3$ and A are as defined above, optionally without isolation of the compounds of the general formulae IV

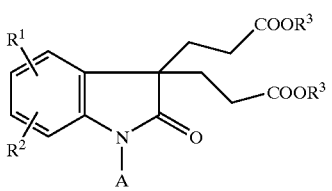

and/or

V

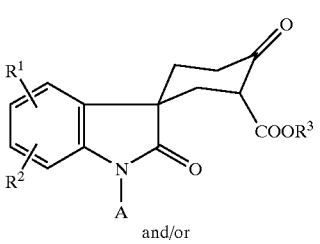

and/or

VI

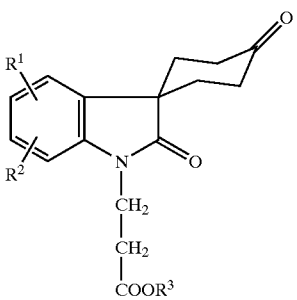

As for compounds capable to introduce the A protective group 2,3-dihydropyrane, triethyl orthoformate or an acrylic acid $C_{1-4}$ester can be applied.

The reaction of the compound of general formula II

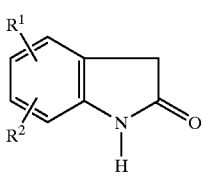

—wherein $R^1$ and $R^2$ are as defined above—with the compound capable to introduce the A protective group is preferably carried out in the presence of a catalyst, preferably in the presence of ptoluenestilfonic acid. As for solvent halogenated hydrocarbons, preferably dichioromethane can be used.

The reaction of the compounds of general formulae II

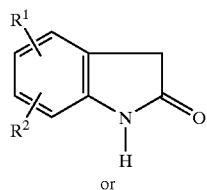

or

III

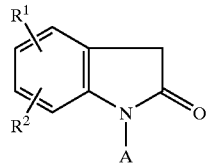

—wherein $R^1$, $R^2$ and A are as defined above—with the acrylic acid $C_{1-4}$ester is carried out in the presence of a catalyst, preferably in the presence of an alkali alcoholate, favorably sodium alcoholate.

Cyclization of the compounds of general formula IV

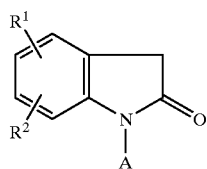

is carried out in the presence of an alkali alcoholate, preferably in the presence of sodium ethylate, potassium t-butylate.

Using acrylic acid $C_{1-4}$ester for protective group, the process can advantageously performed as a "one pot" method, in a polar solvent, in the presence of a base.

Compounds of the general formulae III,

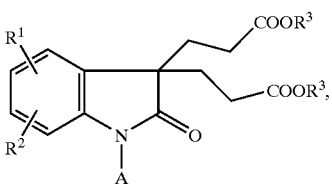

IV

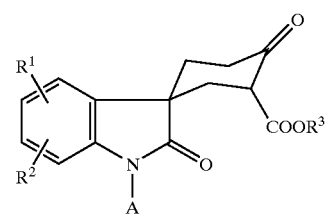

V and

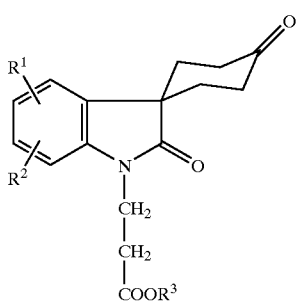

—wherein $R^1, R^2, R^3$ and A are as defined above—are new compounds, with the proviso, that in compound IV, if $R^1$ and $R^2$ stand for hydrogen, A is different from methoxycarbonylethyl group.

Further details of the invention are demonstrated by the following examples, without limiting the claims to the examples.

EXAMPLES

1./ To 38.33 g of 5-ethoxy-indan-2-one 2.12 g of p-toluenesulfonic acid and 880 ml of dichloromethane are added, then under stirring 59 ml of dihydropyrane. The reaction mixture is stirred until complete dissolution (approx 2 hours), then it is allowed to stand for 36 hours. The resulting brown solution is washed with 8% aqueous sodium hydrogencarbonate solution, dried over sodium sulfate and evaporated. The residue is slowly poured into 500 ml of petroleum ether. The resulting precipitate is filtered off, washed with a small amount of petroleum ether. Thus, 42.4 g of 1-(2-tetrahydropyranyl)-5-ethoxy-indolin-2-one is obtained, mp.: 108–110° C. Yield: 75%

To 41.8 g of 1-(2-tetrahydropyranyl)-5-ethoxy-indolin-2one, 1.2 g of sodium ethylate and 440 ml of toluene are added. To the resulting solution 34 ml of ethyl acrylate is added slowly, under stirring, at 25° C., in a period of 4 hours. The reaction mixture is stirred for additional 2 hours, then it is washed with 8% aqueous sodium hydrogencarbonate solution, dried over sodium sulfate, clarified with active carbon, filtered and concentrated in vacuo.

The residue is slowly poured into 250 ml of petroleum ether. The resulting solid material is filtered off, washed with petroleum ether. 58 g of 1-(2-tetrahydropyranyl)-3-(di-/ethoxycarbonylethyl)-5-ethoxy-indolin-2-one is obtained, mp.: 84–86° C. Yield: 78%.

178 g of 1-(2-tetrahydropyranyl)-3-(di-/ethoxycarbonylethyl/)-5-ethoxy-indolin-2-one in 1300 ml of toluene is stirred with 60.4 g of sodium ethylate and 6 of tetrabutylammonium bromide at 55° C. for 3,5 hours. After cooling the reaction mixture is extracted consecutively with 300 ml of ice-cold water, 300 ml of 1 N hydrochloric acid, and 150 ml of water, clarified with active carbon and Fuller's earth, and filtered. The filtrate is evaporated in vacuo, the residue is heated under stirring at reflux temperature for 3.5 hours in the mixture of 790 ml of 50%-ethanol and 315 ml conc. hydrochloric acid. The mixture is then poured into 3000 ml of water, the aqueous phase is extracted with 2×600 ml and 3×300 ml of toluene, dried over sodium sulfate, evaporated in vacuum. The residue is crystallized in diisopropyl ether. The resulting material is filtered off, washed with diisopropyl ether. Thus 60.1 g of spiro[(4-cyclohexanone)-1,3'(5'-ethoxy)-[3H]indol-2'[1'H]-one is obtained, mp.: 171–172° C. Yield: 60%.

2./ Into 318 ml of dimethyl sulfoxide 112.7 g of 5-ethoxy-indan-2-one is added, then, under stirring, 3.82 g of potassium t-butylate. To that suspension, after 10 minutes of stirring, 172.1 g of methyl acrylate is added, dropwise, at a temperature of 40–45° C., in a period of 70 minutes. The mixture is stirred at that temperature for additional 65 minutes, then to it is added 161 g of potassium t-butylate, in a period of 30 minutes, while keeping the temperature below 60° C. The t-butanol is distilled off, the thick residue is poured into 1780 ml of water, the solution is clarified with active carbon and filtered. The filtrate is stirred in a 85° C. bath. When it reaches the 68° C. (approx. 25 min.) it is seeded, then stirring is continued for additional 3 hours, at a temperature of max. 81° C. The mixture is then cooled to room temperature, the resulting precipitate is filtered off and washed thoroughly with water. Thus, 110.7 g of spiro[(4-cyclohexanone)-1,3'(5'-ethoxy)-[3H]indol-2'[1'H]-one is obtained, mp.: 184 –186 ° C., it suitable for the next step. Yield: 67%.

3./ 11.2 g of 5-ethoxy-indan-2-one and 220 ml of triethyl orthoformate are stirred at 135–140° C. for 20 hours, then the reaction mixture is evaporated in vacuo. 17.2 g of 1-(diethoxy-methylene)-5-ethoxy-indolin-2-one is obtained as an oil. Its structure was proved by NMR spectroscopy. Yield: 92%.

To the mixture of 17.2 g of 1-(diethoxy-methylene)-5-ethoxy-indolin-2-one, 1.5 g of potassium t-butylate and 170 ml of toluene 12.6 ml of ethyl acrylate is added dropwise, at 20–30° C., in a period of 1 hour. After additional 90 minutes of stirring 50 ml of water is added to the reaction mixture, the phases are separated, the organic phase is washed with water, dried over sodium sulfate, evaporated in vacuum. 22.2 g of 1-(diethoxy-methylene)3-(di-/ethoxycarbonylethyl/)-5-ethoxy-indolin-2-one is obtained in the form of yellow-brown crystallizing oil, which is crystallized from 110 ml of n-hexane. 15.1 g crystalline product is obtained, mp: 82–83° C. Yield: 62%.

15 g of 1-(diethoxy-methylene)-3-(di-/ethoxycarbonylethyl/)-+5-ethoxy-indolin-2-one is dissolved in 150 ml of toluene, and to the solution 7.2 g of potassium-t-butylate is added under stirring, in 10 minutes. The reaction mixture is stirred at room temperature for 2 hours, then water is added to it, the phases are separated, the organic phase is washed with water, dried over sodium sulfate, evaporated in vacuum. Thus, 10.2 g of spiro[(3-ethoxycarbonyl-4-cyclohexanon)-1,3'(1'-diethoxy-methylene-5'-ethoxy)-[3H]indol]-2'-one is obtained in the form of a brown oil, its structure was proved by NMR spectroscopy. Yield: 76%.

4,05 g of spiro[(3-ethoxycarbonyl-4-cyclohexanon)-1,3' (1'-diethoxy-methylene-5'-ethoxy)-[3H]indol-2'-one is stirred for 2 hours at room temperature in the mixture of 20 ml of 96% ethanol and 0,5 ml of 2N hydrochloric acid, the reaction mixture is then cooled with ice-water to 5° C. The precipitating spiro[(3-ethoxycarbonyl-4-cyclohexanon)-1,3' (1'-formyl-5'-ethoxy)-[3H]indol]-2'-one is filtered off, mp.: 133–136° C. Yield: 52%.

5 g of spiro[(3-ethoxycarbonyl-4-cyclohexanon)-1,3'(1'-formyl-5'-ethoxy)-[3H]indol]-2'-one is dissolved in 100 ml of acetic acid, 25 ml of 5N sulfuric acid is added to it. The mixture is refluxed under stirring, then it is evaporated in vacuum. To the residue water is added, the pH is adjusted to pH 7 with sodium hydroxide solution. 3.1 g of solidifying oil precipitates is obtained, which is identical with the spiro[(4-cyclohexanon)-1,3'(5'-ethoxy)-[3H]indol]-2'[1'H]-one obtained by another route. Mp.: 139–140° C. Yield: 86%.

What is claimed is:

1. A process for the preparation of spiro[(4-cyclohexanone)-[3H]indol]-2'[1'H]-one derivatives of the general formula I

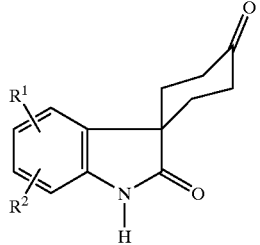

—wherein $R^1$ and $R^2$ independently stand for hydrogen, $C_{1-4}$alkyl, $C_{1-4}$alkoxy, $C_{1-4}$alkylthio, $C_{1-4}$polyfluoroalkyl, $C_{1-4}$polyfluoroalkoxy, $C_{3-7}$cycloalkyloxy, $C_{3-7}$cycloalkylthio, phenoxy, benzyloxy or nitro group which comprises reacting an indolin-2-one derivative of the general formula II

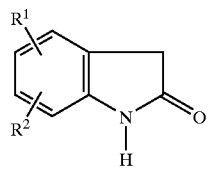

—wherein $R^1$ and $R^2$ are as defined above—with a compound selected from 2,3-dihydropyrane, triethylorthoformate or acrylic acid $C_{1-4}$ester capable for introducing a protective group, selected from 2-tetrahydropyranyl, 1-diethoxy-methylene or $C_{1-4}$alkoxycarbonylethyl group to produce a compound of general formula III,

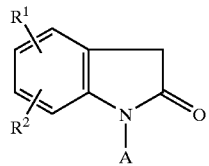

coupling the compound of general formula III, thus obtained—wherein $R^1$ and $R^2$ are as defined above and A stands for a protective group, selected from 2-tetrahydropyranyl, 1-diethoxy-methylene or $C_{1-4}$alkoxycarbonylethyl group—with an acrylic acid $C_{1-4}$ester to produce a compound of formula IV, cyclizing the resulting compound of the general formula IV

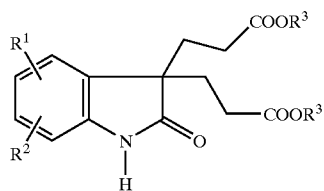

—wherein $R^1$, $R^2$ and A are as defined above, $R^3$ stands for $C_{1-4}$alkyl group—, to produce a compound of general formula V and eliminating the —$COOR^3$ group and the A protective group of the keto-ester of general formula V to produce a compound of general formula I

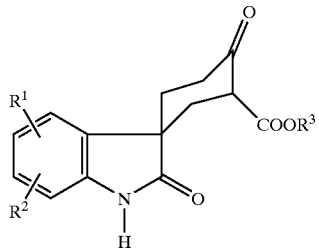

wherein $R^1$, $R^2$, $R^3$ and A are as defined above, optionally without isolation of the compounds of the general formulae IV

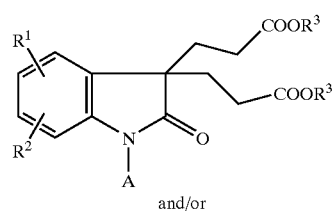

and/or

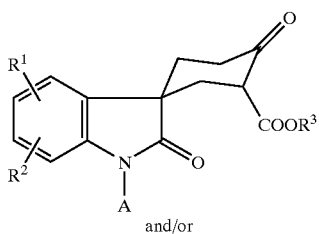

and/or

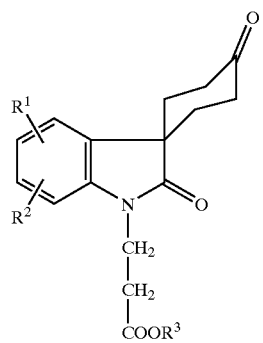

2. A process according to claim 1 which comprises carrying out the reaction of the compound of the general formula II

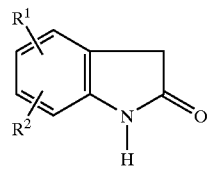

—wherein $R^1$ and $R^2$ are as defined in claim 1 with a compound selected from 2,3-dihydropyrane, triethylorthoformate or acrylic acid $C_{1-4}$ester capable for introducing the A protective group—wherein A is as defined in claim 1 in the presence of a catalyst.

3. A process according to claim 1 which comprises carrying out the reaction of the compound of the general formula III

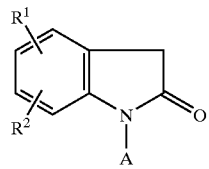

—wherein $R^1$, $R^2$ and A are as defined in claim 1—with an acrylic acid $C_{1-4}$ ester in the presence of a catalyst.

4. A process according to claim 2 which comprises using as catalyst an acidic catalyst or an alkaline catalyst.

5. A process according to claim 3 which comprises using as catalyst an alkaline catalyst.

6. A process according to claim 4 which comprises using as the catalyst p-toluenesulfonic acid or an alkali alcoholate.

7. A process according to claim 5 which comprises using as the catalyst an alkali alcoholate.

\* \* \* \* \*